United States Patent [19]

Seppi

[11] Patent Number: 4,875,487

[45] Date of Patent: Oct. 24, 1989

[54] COMPRESSIONAL WAVE HYPERTHERMIA TREATING METHOD AND APPARATUS

[75] Inventor: Edward J. Seppi, Menlo Park, Calif.

[73] Assignee: Varian Associates, Inc., Palo Alto, Calif.

[21] Appl. No.: 860,281

[22] Filed: May 2, 1986

[51] Int. Cl.$^4$ .................... A61B 8/00; A61N 5/00
[52] U.S. Cl. ......................... 128/660.03; 128/399
[58] Field of Search ................ 128/399, 24 A, 804, 128/660, 660.03

[56] References Cited

U.S. PATENT DOCUMENTS

| | | | |
|---|---|---|---|
| 3,958,559 | 5/1976 | Glenn et al. | 128/24 A |
| 4,210,152 | 7/1980 | Berry | 128/804 X |
| 4,368,410 | 1/1983 | Hance et al. | 128/24 A |
| 4,397,313 | 8/1983 | Vaguine | 128/804 X |
| 4,441,486 | 4/1984 | Pounds | 128/24 A |
| 4,484,569 | 11/1984 | Driller et al. | 128/24 A X |
| 4,526,168 | 7/1985 | Hessler et al. | 128/24 A X |
| 4,549,533 | 10/1985 | Cain et al. | 128/24 A |
| 4,582,065 | 4/1986 | Adams | 128/660 |
| 4,586,512 | 5/1986 | Do-Huu | 128/660 |
| 4,620,546 | 11/1986 | Aide et al. | 128/660 |
| 4,622,972 | 11/1986 | Grebeler Jr. | 128/399 |
| 4,646,756 | 3/1987 | Watmough et al. | 128/804 |
| 4,658,828 | 4/1987 | Dory | 128/660 |

FOREIGN PATENT DOCUMENTS 3150513  6/1983  Fed. Rep. of Germany ...... 128/399

OTHER PUBLICATIONS

Fessenden et al., "Experience ... Deep Tissue", IEEE Trans. Bio. Med. Eng., vol. 31, No. 1, Jan. 1984, pp. 126-135.
Marmor et al., "Treating ... Hyperthermia", Int. J. Rad. Onc. Biol. Phys. vol. 4, pp. 967-973, 1978.
Seppi et al., "A Large Aperture Ultrasonic Array ... ", 1985, Ultrasonics Symp., vol. 2, pp. 942-948, Oct. 1985.

Primary Examiner—Lee S. Cohen
Attorney, Agent, or Firm—Stanley Z. Cole; Gerald M. Fisher; Terrence E. Dooher

[57] ABSTRACT

A wide bandwidth compressional wave transducer array obtains information concerning tissue of a subject being treated and supplies hyperthermia compressional wave treating energy to a treated region of the subject. The array transducers are pulsed on and off with an on duty cycle portion of less than one. An array of compressional wave imaging transducers is in the center of the array of compressional wave hyperthermia focused far field transducers used to analyze and treat. The power and duty cycle of the compressional wave hyperthermia focused far field are varied to control the energy incident on certain regions in a treated subject. The ultrasonic frequencies of hyperthermia beams derived from individual transducers are randomly angle modulated so the energy of adjacent far field focused beams overlaps to a greater extent than focused coherent beams.

15 Claims, 4 Drawing Sheets

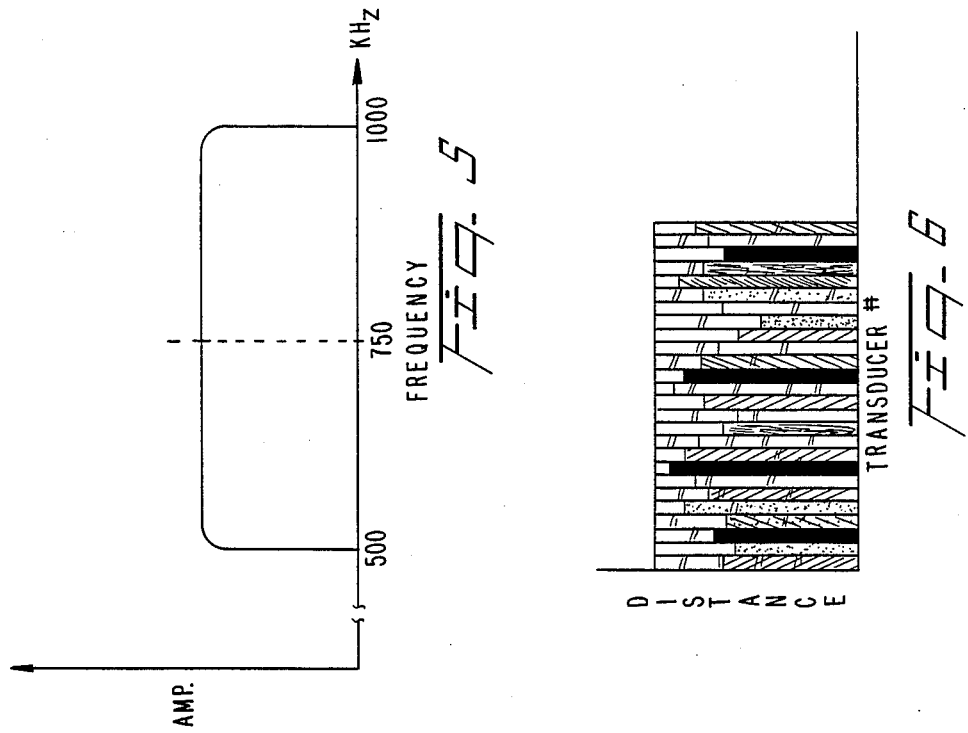
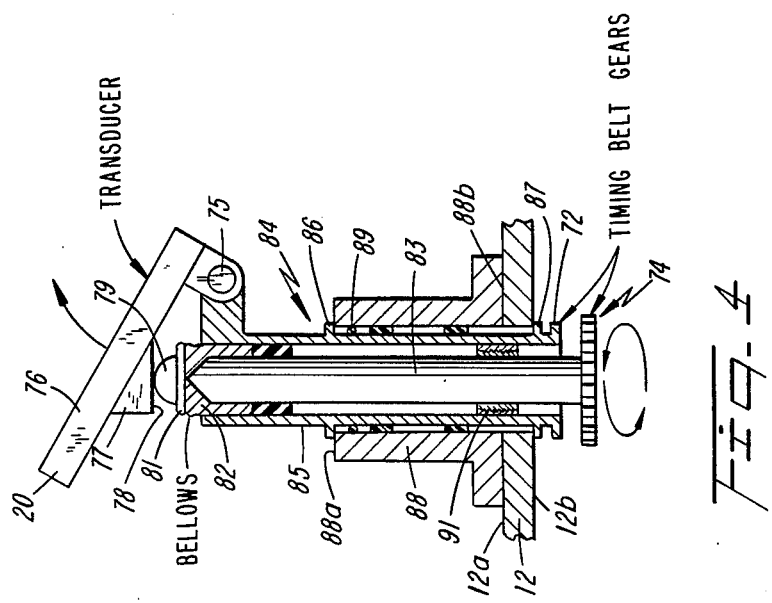

COMPRESSIONAL WAVE HYPERTHERMIA TREATING METHOD AND APPARATUS

TECHNICAL FIELD

The present invention relates generally to hyperthermia compressional wave treating methods and apparatus utilizing focused far fields. In one aspect of the invention, a wide bandwidth compressional wave transducer array is used to obtain information concerning tissue of a subject being treated and to supply hyperthermia compressional wave treating energy to a treated region of the subject. In another aspect of the invention, transducers of an array that produces hyperthermia compressional wave focused far fields are pulsed on and off with an on duty cycle portion of less than one. In still another aspect of the invention, an array of compressional wave hyperthermia focused far field producing transducers is combined with an array of compressional wave imaging transducers. In a further aspect of the invention, a patient is analyzed with compressional wave energy by imaging transducers in the center of an array of compressional wave hyperthermia focused far field transducers that is used to analyze and treat. In an additional aspect of the invention the power and duty cycle of an array of compressional wave hyperthermia focused far field transducers are varied to control the energy incident on certain regions in a treated subject. In a still further aspect of the invention the ultra sonic frequencies of beams derived from individual transducers of a focused far field compressional wave hyperthermia treating array are randomly angle modulated to generate beams having incoherent spatial variations and more constant energy distribution between adjacent beams.

BACKGROUND ART

It is known that relatively intense compressional wave energy in a focused far field of an ultrasonic transducer array can be used for therapeutic purposes. The ultrasonic focused far field compressional wave energy produces hyperthermia effects to raise the temperature of treated malignant tissue sufficiently to destroy same. Typically, the array transducers are excited with frequencies in the 0.5–2 megahertz region.

In the past, the array transducers have typically been narrow bandwidth resonant devices, effective over only a narrow frequency band, e.g., 50 kilohertz. The transducers have been excited at a frequency that is approximately equal to the resonant frequency thereof to provide greatest efficiency between an electric energy source and the transducers. Hence, the treating transducers have generally been driven at a single frequency or frequencies in a very narrow band. The ultrasonic energy derived from the transducers is coupled directly by contact to the skin of the subject or is coupled indirectly to the subject by way of a compressional wave transmitting liquid, such as water.

Because of the single frequency or narrow band width excitation and the narrow band width characteristics of the prior art transducer arrays, single arrays formed of such transducers have not been well adapted to efficiently and effectively treat both shallow and deep regions, i.e., regions which are respectively close to and far from the surface of the skin of the subject where the focused far field hyperthermia compressional wave energy enters the subject. For the most efficient and effective treatment, the frequency of the compressional wave energy is inversely related to the depth of the treated region so that deep regions are treated with low frequency energy and vice versa for shallow regions. Narrow bandwidth arrays do not have adequate bandwidth to couple energy efficiently and effectively to deep and shallow regions.

The narrow bandwidth treating arrays are not particularly well adapted for both diagnostic and hyperthermia treating purposes. Most diagnostic ultrasonic compressional wave systems utilize echo techniques wherein an ultrasonic compressional wave energy pulse is derived from a transducer, transmitted to the subject and reflected from interior regions of the subject back to the same transducer which derived it. The travel time of the ultrasonic compressional wave pulse, from the time it leaves the transducer until the time the reflected energy is coupled back to the transducer, is a measure of the location of a region of interest in the body of the subject. Typically, the regions of interest are bones, air pockets in the subject, various body organs and malignant regions. The amplitude of the reflected energy incident on the transducer provides an indication of the nature of the reflecting region in the subject.

When a narrow bandwidth transducer, e.g., as employed in prior art hyperthermia devices, is supplied with a pulse of electric energy, the transducer typically "rings" in a manner similar to a shock excited resonant circuit to derive a sequence of damped sine wave like oscillations at the transducer natural frequency. If a typical prior art narrow band width transducer previously employed for hyperthermia treatment purposes were pulsed to enable a reflected pulse to be coupled back to it for diagnostic purposes, the transducer would still be ringing at the time the reflected energy is coupled back to the transducers. If a transducer is ringing when the reflected energy is coupled back to it, the transducer does not derive an accurate replica of the reflected energy wave incident thereon. Hence, little or no information can be derived for diagnostic purposes with the narrow bandwidth transducer arrays previously employed for hyperthermia treating purposes.

It is, accordingly, an object of the present invention to provide a new and improved apparatus for and method of utilizing ultrasonic compressional wave energy for hyperthermia treating and diagnostic purposes.

Another object of the invention is to provide a new and improved apparatus for and method of hyperthermia treating and analyzing a subject with ultrasonic compressional wave energy derived from the same transducers of an electric energy - compressional wave energy transducer array.

Another object of the present invention is to provide a new and improved apparatus for and method of treating deep and shallow regions of a subject with compressional wave energy derived from the same transducers of a compressional wave transducer array.

Presently developed ultrasonic compressional wave hyperthermia treating arrays emit continuous wave beams having relatively low power levels such that there is approximately a linear relationship between the heating effect at the focused far field treated area and the beam instantaneous power or intensity. A problem with such ultrasonic compressional wave hyperthermia treating arrays is that the subject, typically a human patient being treated for destruction of cancerous tumors, is subjected to considerable pain when a beam from an array transducer is incident on certain untreated areas. Typically the pain occurs because a bone is in a beam path from a particular transducer in the array. The irradiated bone is frequently remote from the region on which the far field is focused. However, it may be proximate the focused far field region. Because of the bone pain problem and the need to limit the maximum amount of energy that can be applied to a treated region where the far fields of several beams are focused, the power of the continuous hyperthermia compressional wave energy in each beam must be limited. To prevent pain, the power in beams incident on such bones must be smaller than the power in the remaining beams.

It is accordingly still another object of the invention to provide a new and improved compressional wave hyperthermia treating system and method using a far field focused transducer array that is activated so as to reduce the amount of pain that a subject experiences during treatment.

A still further object of the invention is to provide a new and improved compressional wave hyperthermia treating system and method using a far field focused transducer array that is activated so that the effective power level applied to a treated area is increased without exceeding the permissible energy level that can be safely applied to the treated region.

DISCLOSURE OF INVENTION

In accordance with one aspect of the invention, the ultrasonic compressional hyperthermia wave energy incident on the subject is maintained within the same safe level as the prior art but the effect thereof is increased many times. This is achieved by increasing the power or intensity of the compressional wave hyperthermia energy and by simultaneously causing it to be transmitted from the array in bursts, rather than continuously; each burst includes several cycles of the compressional wave hyperthermia energy. The duty cycle and power or intensity levels are inversely related so that the compressional wave energy, equal to the product of the duty cycle and power levels, is approximately constant.

The effectiveness of the hyperthermia energy increases with the temperature of the tissue at the treatment site. The temperature of tissue at the treatment site is a complex matter since body cooling mechanisms come into play. However an important determinant of temperature at the treatment site is the efficiency with which the hyperthermia wave energy is converted into heat. In the continuous wave case, the efficiency of conversion or absorption increases in a nonlinear manner as the power increases. In particular, for higher levels within the range of interest for treating tumors, the conversion efficiency and hence the temperature at the tumor site, tends to increase as a power, $\alpha$, greater than one of the power of the wave. For heuristic purposes we assume alpha equals two, so that, for example, if the power increases from one unit to two units the temperature at the tumor site would tend to increase from one unit to four units.

Due to this power principal, when the energy is supplied in bursts, the effectiveness of treatment, i.e., the temperature at the tumor site, may be increased without increasing the average energy supplied. For example, if the duty cycle is 0.5, a wave having a power level of two units during the "ON" portion of the duty cycle provides a higher temperature than a continuous wave having a power level of one unit even though the average power is the same.

The level of pain produced at a pain site, remote from the tumor site also increases with temperature. However, pain increases slowly as a function of temperature until the temperature reaches a threshold temperature above which the pain tends to increase rapidly. The increased coupling or conversion efficiency obtained using wave energy having higher maximum power supplied in bursts, i.e. a duty cycle less than one, may also tend to increase the temperature at the pain site. However as long as the temperature at the pain site remains below the threshold temperature the patient does not experience an appreciable increase in pain even though the effectiveness of treatment is increased substantially. When the pain site is further from the source of the hyperthermia wave energy than the treatment site the increased absorption of wave energy at the treatment site using wave energy having increased maximum power and a duty cycle less than one leaves a lesser amount of wave energy to be absorbed at the remote pain site. This tends to decrease or to mitigate the temperature increase at the pain site.

The non-linear effect of power and effectiveness in ultrasonic compressional wave hyperthermia treatment is known in the continuous wave case. However, in the prior art the continuous wave power incident on a particular region has been increased by focusing techniques, rather than by use of pulse width, duty cycle techniques and apparatus. The pulse width, duty cycle technique and apparatus has considerably greater flexibility than the focusing technique because the average power and burst power levels can both be controlled. As pointed out supra controlling average and burst power levels enables the effectiveness of the hyperthermia and/or control of pain to be attained.

In accordance with a further aspect of the present invention, a region of a subject is treated with hyperthermia compressional wave energy derived from an array of wide bandwidth ultrasonic transducers. To treat shallow regions of the subject which are close to the skin of the subject where the energy enters the body, the transducers of the array are supplied with relatively high frequency energy. To treat deep regions in the subject, the same transducers are excited with relatively low frequency energy. Because the array transducers have a wide bandwidth, capable of handling both the high and low frequencies with about the same efficiency, the amplitude of the high and low frequency energy derived from the transducers is approximately the same, whereby the surface and deep regions are treated with about the same efficiency and effectiveness. The array is arranged and excited so that treating ultrasonic far field compressional wave energy derived from the transducers is focused on the treated region. Pounds U.S. Pat. No. 4,441,486, and the copending Giebeler application Ser. No. 418,136, commonly assigned with the present invention, filed Sep. 15, 1982, now U.S. Pat. No. 4,622,972, discuss far field hyperthermia ultrasonic compressional wave treatment of a subject, and are incorporated herein by reference.

In accordance with another aspect of the invention, transitions between adjacent focused regions are blurred and made to have approximately the same intensity as regions close to the boresight axes of the focused beams by slightly defocusing the beams derived from the array. To this end the electric energy applied to the transducers is randomly angle (i.e., frequency or phase)

modulated, which randomly frequency or phase shifts the array compressional wave energy to cause the derivation of spatially incoherent beams. The spatially incoherent beams from the different transducers spread the beam energy in the treated region, so that abrupt edges of spatially adjacent beams from the individual transducers are avoided.

Because the treating transducers have a wide band frequency response, they can be supplied with pulse like energy without substantial ringing. Thereby, the same wide bandwidth transducers for treating the subject can be utilized for analyzing the subject. Pulses or single sine wave like cycles of electric energy having frequency components predominantly in the transducer band pass are supplied in sequence to individual transducers of the array. Each transducer responds to the pulse or single cycle sine wave to emit a single sine wave cycle of compressional wave energy that is coupled to the subject. Because the transducer has a wide bandwidth i.e., low quality factor or Q, the transducer does not ring in response to the pulse or single cycle electric energy supplied to it. Each activated transducer responds to energy reflected from a site in response to the pulse or single cycle sine wave to derive an electric signal that is an accurate replica of the reflected compressional wave energy incident on it.

The signal derived from each transducer is processed to derive an indication of the location of a reflection site in the subject. An indication of the reflected energy power level is obtained from the replicas derived from the treating array transducers. Signals derived from the replicas are supplied in sequence to a so called multi-B-scan scope, wherein the number of each sequenced transducer is plotted along an X axis direction, the distance of the reflecting site from the array is plotted along a Y axis direction, and the intensity of the response from each transducer is indicated by the brightness of a bar extending in the Y direction.

In accordance with a further aspect of the present invention, the wide band width transducer array of treating transducers is combined with an array of one circular and several annular imaging transducers. The wide band transducers are arranged in several ringlike groups about a boresight axis for the array. Concentric with the boresight axis and in the center of the treating transducers are the concentric circular and annular imaging transducers that are mechanically scanned. The treating transducers are focused on a region to be treated by moving them back and forth along a z-axis, i.e., an axis along the boresight axis, as well as in two directions in a plane generally parallel to the surface of the skin of the subject being treated. The relative angle of the transducers to the boresight axis is also controlled to vary the diameter of the focused far field.

It is, accordingly, a further object of the present invention to provide new and improved compressional wave hyperthermia treating transducer array in combination with an ultrasonic compressional wave imaging transducer array.

An additional object of the present invention is to provide a new and improved compressional wave treating, analyzing and imaging array which is controlled to facilitate setup of the treating transducers prior to and during treatment.

An additional object of the invention is to provide a new and improved method of and apparatus for controlling compressional wave energy emitted by plural transducers of an array having a focused far field, so that adjacent regions responsive to different beams of the different transducers in the array are subject to random variations, as is the depth of the focal plane of the combined pattern derived from the transducers of the array.

The above and still further objects, features and advantages of the present invention will become apparent upon consideration of the following detailed description of one specific embodiment thereof, especially when taken in conjunction with the accompanying drawings.

BRIEF DESCRIPTION OF DRAWINGS

FIG. 4 is a side view of a single treating transducer and a rotary drive mechanism therefor in an array illustrated in FIGS. 1 and 2;

FIG. 5 is a plot of intensity versus frequency of the output of a single transducer in the array illustrated in FIGS. 1 and 2;

FIG. 6 is an exemplary B-scan display generated by the apparatus illustrated in FIGS. 1–4.

BEST MODE FOR CARRYING OUT THE INVENTION

Figure 1:
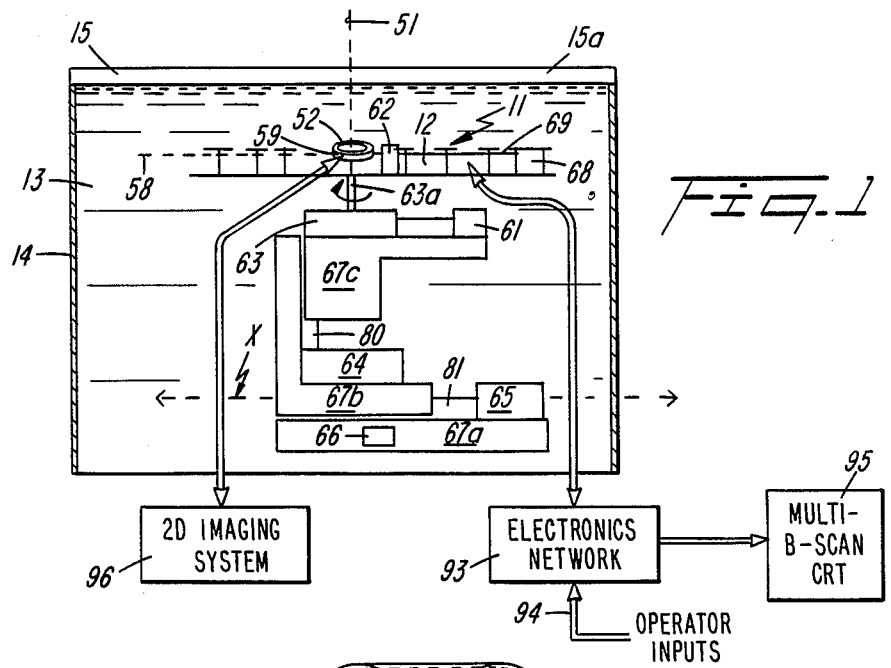
FIG. 1 is a schematic diagram of a preferred embodiment of the apparatus included in the present invention.
Figure 2:
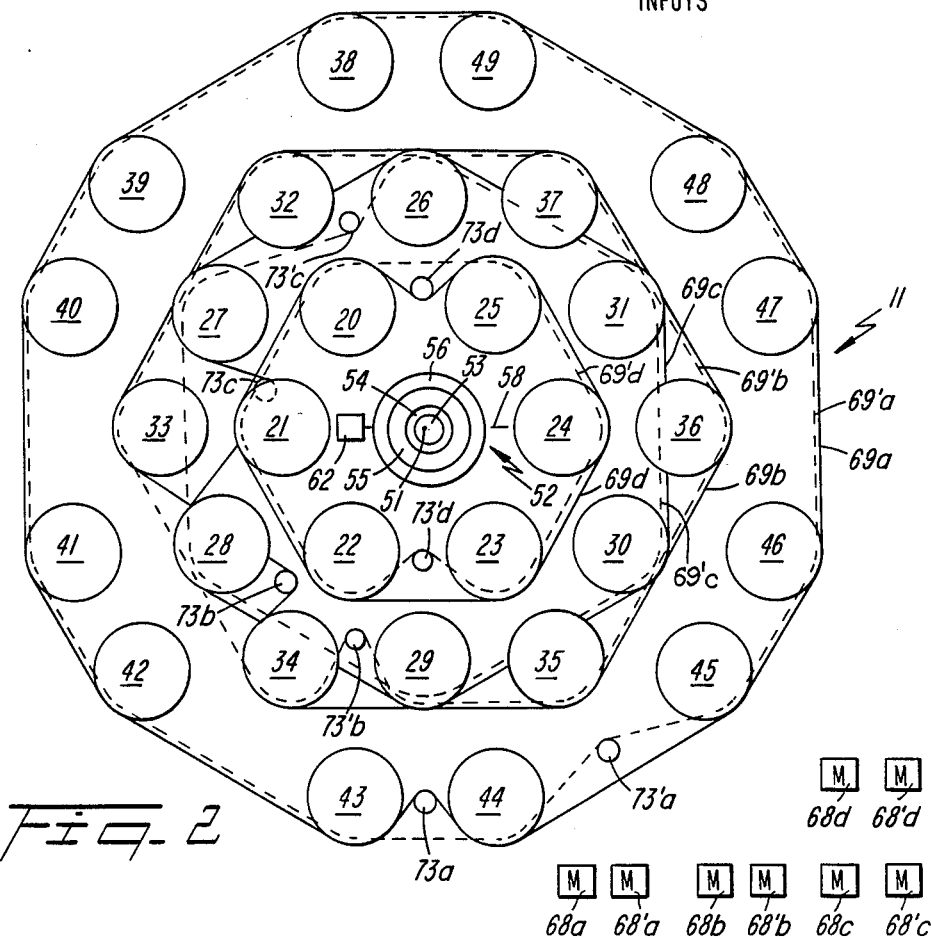
FIG. 2 is a top view of the transducer array included in the apparatus illustrated in FIG. 1.

Reference is now made to FIG. 1 of the drawing wherein there is illustrated ultrasonic electric wave-compressional wave transducer array 11, mounted on platform 12, located in aqueous bath 13, in container 14, having upper surface 15 that is relatively transparent to compressional wave energy. The outside face of surface 15 defines a bearing surface for a patient on a treating couch (not shown). As illustrated in FIG. 2, array 11 includes 30 treating transducers 20–49, having a central boresight axis 51, along which a compressional wave hyperthermia treating far field from the array is derived; for a discussion of compressional wave hyperthermia far field treating, reference is made to Pounds U.S. Pat. No. 4,441,486, and to the previously mentioned commonly assigned now U.S. Pat. No. 4,622,972, which are incorporated herein by reference. Each of transducers 20–49 has a relatively flat amplitude versus frequency response over a wide bandwidth, e.g., 500 kilohertz to 1 megahertz.

Platform 12 is linearly driven along axis 51 and along a pair of axes that intersect with and are at right angles to axis 51 and driven rotationally about axis 51 to control the position of the focused hyperthermia compressional wave far field derived from array 11. Boresight axis 51 passes through the center of array 52 of ultrasonic electric compressional wave imaging transducers 53–56. Transducer 53 is a disk, while transducers 54–56 are annuli with increasing radii. Transducers 53–56 of imaging array 52 are excited with a frequency outside the bandpass of transducers 20–49, e.g., 2.5 megahertz. Array 52 is mounted on gimballed table 59 (FIG. 1) that is carried by platform 12. Table 59 is rotatably driven relative to platform 12 about axis 58, which is orthogonal to and intersects boresight axis 51. Platform 12 is rotatable about axis 51 so that the direction of drive axis 58 can be set as desired. Table 59 is tilted about axis 58 to control the angle relative to axis 51 of the boresight axis of an imaging beam derived from transducers 53-56. The origin of the imaging beam boresight axis is coincident with the intersection of boresight axis 51 and axis 58. To these ends, gimballed platform 59 is driven about axis 58 by motor 62, fixedly mounted on platform 12 and having an output shaft coincident with axis 58.

Platform 12 is driven along boresight axis 51 (i.e., in a vertical, z-axis direction) and along x and y directions that are at right angles to each other in a plane at right angles to axis 51.

Platform 12 is also driven rotationally about boresight axis 51. To these ends, motors 61 and 64-66 are provided. Motor 61 is fixedly mounted on block 67c and drives a worm gear 63, also mounted on block 67c, to rotate shaft 63a, which is connected between table 12 and worm gear 63. The longitudinal axis of shaft 63a is coincident with boresight axis 51 and table 12 rotates with shaft 63a. Motor 64 is fixedly mounted on block 67b and drives a first lead screw 80 having a longitudinal axis parallel to boresight axis 51. One end of lead screw 80 is connected to block 67c to drive block 67c and hence table 12 along the z (boresight) axis. Motor 65 is fixedly mounted on block 67a and drives a second lead screw 81 having a longitudinal axis along an x axis orthogonal to boresight axis 51. One end of lead screw 81 is connected to block 67b to drive block 67b and hence table 12 along the x axis. Motor 66 is fixedly mounted relative to container 14 by a suitable structure (not shown) and drives a third lead screw (not shown) having a longitudinal axis along a y axis orthogonal to the x axis and to boresight axis 51. One end of the third lead screw is connected to block 67a to drive block 67a and hence table 12 along the y axis.

Motors 61 and 64-66 are controlled by operator inputs in a conventional manner to translate platform 12 along the x, y and z axes and to rotate platform 12 about boresight axis 51. Hence, the position of boresight axis 51 is varied by controlling motors 65 and 66, while the vertical position of the focus of arrays 11 and 52 is controlled by motor 64. Motors 64-66 are controlled to determine the region in the subject that is to be treated by the hyperthermia compressional wave energy derived from array 11, as well as the portion of the subject to be imaged by the compressional wave energy derived from array 52. Motor 61 is controlled to determine the angular position of the platform 12 and thus the direction of axis 58 about which the image transducer array 52 is rotated. Motors 64-66 are activated during initial setup to control where the focused hyperthermia compressional wave far field of array 11 is incident on the interior of the body being treated. After motors 64-66 have positioned array 11 at the desired location, and after motor 61 has determined the direction of axis 58, a two-dimensional image of the treated region is obtained by scanning transducers 53-56 of array 52 about axis 58.

Each transducer 20-49 in array 11 has a corresponding acoustic lens (not shown) placed over its upper face to focus the beam from the corresponding transducer. Each lens is easily removable and exchangeable with another lens of different type so different focusing characteristics can be obtained. In one embodiment all the focusing lenses have the same focal length. It is preferred that each acoustic lens not tightly focus the beam from its transducer so that the energy in the beam is diffused over a relatively large focal plane. The location of the minimum diameter of the envelope of coherent beams along the boresight axis 51 from the transducers in array 11 is principally controlled by changing the tilt angles of transducers 20-29 relative to the plane of platform 12. The tilt angles are controlled by simultaneously driving all of the transducers in array 11 by motors 68'a-68'd via gears 73'a-73'd, which drive timing belts 69'a-69'd respectively, while timing belts 69a-69d and gears 73a-73d remain motionless. To this end, motors 68'a-68'd are fixedly mounted on platform 12 and are coupled via a suitable gear train (not shown) to gears 73'a-73'd respectively which drive belts 69'a-69'd, respectively, which as a group engage all of the transducers 20-49 in array 11.

The degree of array focusing, in particular the minimum diameters of the envelope of coherent beams from the transducers in array 11, is principally controlled by simultaneously driving each of the transducers in array 11 rotationally through the same angle about an axis (for each transducer) that is at right angles to the planar platform 12. To this end, motors 68a-68d drive gears 73a-73d respectively and belts 69a-69d, respectively, which as a group engage all of the transducers in array 11. The above array focusing processes are described subsequently in more detail in conjunction with FIG. 4. In either process for controlling the array focusing, the control of motors 68a-68d and motors 68'a-68'd (denoted collectively by motor 68 in FIG. 1) and belts 69a-69d and 69'a-69'd is in response to an operator input, during initial setup, through the use of conventional motor control circuitry.

Transducers 20-49 of array 11 are arranged in four separate rings concentric with boresight axis 51. Transducers 20-25 are on a first ring that is closest to boresight axis 51, transducers 26-31 are on a second ring which is farther from boresight 51 than the first ring, transducers 32-37 are on a third ring that is further from axis 51 than the second ring including transducers 26-31, and transducers 38-49 are on a ring that is most remote from the boresight axis. As shown in FIG. 2, two motors, two drive belts and two gears are provided for each of the transducer rings in FIG. 2. For example, motors 68d and 68'd for driving drive belts 69d and 69'd and corresponding gears 73d and 73'd are provided for the first ring of transducers 20-25.

The mechanism for controlling the tilt angle of one of the transducers of array 11 relative to axis 51 is illustrated in FIG. 4. FIG. 4 also illustrates the mechanism for controlling the rotation of this transducer about an axis perpendicular to the plane of platform 12. For purposes of illustration, transducer 20 is considered in connection with FIG. 4, but it is to be understood that the drive mechanism for each of transducers 20-49 is the same as that illustrated in FIG. 4.

Fixedly mounted on the bottom face of transducer 20 is triangular wedge 77, having a bottom, planar face 78 engaging an upper portion of hemisphere 79, which is fixedly mounted on horizontally extending plate 81 at the top of bellows 82. Hemisphere 79, plate 81 and bellows 82 are vertically driven in response to shaft 83 being turned by belt 69d via gear 74, at the bottom of the shaft while belt 69'd remains motionless, preventing gear 72 from turning. Concentric with shaft 83 is assembly 84, fixedly mounted to platform 12, and on which pin 75 is mounted. Assembly 84 includes sleeve 85, having lower and upper flanges 87 and 86 respectively captured by the lower, horizontal face 12b of platform 12 and the upper, horizontally extending face 88a of collet 88 having a lower, horizontally extending planar face 88b which is fixedly mounted on the upper face 12a of platform 12. Collet 88 has an inner diameter that is spaced from the outer diameter of sleeve 85; O-ring seal 89 is in the gap between the inner diameter of collet 88 and the outer diameter of sleeve 85 to prevent liquid from seeping into the gap. A gap is also provided between the inner diameter of sleeve 85 and the periphery of shaft 83. Shaft 83 and sleeve 85 are, however, interconnected by threads 91 so that the shaft turns relative to the sleeve in response to gear 74 being driven by belt 69'd while belt 69'd engages gear 72 on sleeve 85 to prevent sleeve 85 from rotating. In response to gear 74 being driven by belt 69'd, while sleeve 85 is held fixed, shaft 83 is turned relative to stationery sleeve 85, causing the shaft to be vertically driven relative to the sleeve. Because pin 75 is fixedly mounted on sleeve 85, wedge 77 and transducer 20 are driven about the pin by shaft 83 being raised and lowered in response to shaft 83 being turned in the clockwise and counterclockwise directions.

Transducer 20 may be driven rotationally about the longitudinal axis of shaft 83 without changing its tilt angle. To this end, motor 68'd drives gear 73'd and belt 69'd, while motor 68d drives gear 73d and belt 69d, and belt 69d and belt 69'd engaging gears 74 and 72 respectively so that gears 72 and 74 turn through the same angle.

In one embodiment the array is initialized so that the center line of the focused beam from each transducer 20-49 passes through a selected point on the boresight axis. Thus the acute angle between the boresight axis and the center line of each beam is the same for all of the beams from a given ring, but decreases from the outermost ring to the innermost ring. This causes most of the energy derived from array 11 to be focused in a prolate spheroid configuration through which the focal plane of the array passes. The transducers in each ring are then rotated so that the distance from the selected point on the boresight axis to the point of intersection of the center line of each beam with the plane passing through the selected point and parallel to the plane of platform 12 is the same for the beams from all transducers. This eliminates the "hot spot" which would otherwise occur at the selected point. It causes most of the energy derived from array 11 to be focused in a cylindrical shell or ring like configuration through which the array focal plane passes. If the transducers in each ring are rotated so that the distance from the selected point on the boresight axis to the point of intersection of the center line of each beam from a given ring with the plane passing through the selected point and parallel to the plane of platform 12 is constant for the beams from the transducers of a given ring, but a different constant for transducers from different rings, a more uniform distribution of energy in the heating region is obtained. This causes most of the energy from array 11 to be focused in an oblate spheroid configuration through which the array focal plane passes.

In the above embodiment motors 68'a through 68'd and belts 69'a-69'd and gears 73'a-73'd are not present and each transducer shaft 83 and sleeve 85 form a unitary rotatable shaft which, for the example shown in FIG. 4, is rotated by motor 68 driving belt 69d which engages gear 74.

In another embodiment (not shown) individual motors are provided for each transducer so that each transducer may be rotated and tilted independently. This embodiment enables one to change the direction of the boresight axis. Focusing the different transducers in the different rings so the focused far fields derived from them have different diameters can be accomplished by providing slightly different gear drive for gears 74 or the gear trains connected to them. Varying the energy distribution over a focal region so that it is not concentrated is therapeutically useful in controlling the distribution of heat across a treated area, such as a tumor. The transducers in the four rings can be focused with respect to each other to change the diameter of an aperture illuminated by the energy derived from the transducers; that is, the focus of the entire array can be varied to control the manner in which the energy is distributed. In one particular embodiment, the array energy can be focused over a diameter range from 1.5 to 12 centimeters; if focused far field uniformity is not particularly important the diameter can even exceed 12 centimeters.

Returning to the description of FIG. 1, signals are supplied to and derived from the transducers of array 11 via electronics network 93, also responsive to various operator inputs from source 94; the inputs from source 94 are associated with initial setup, the duty cycle of the AC treating energy supplied to the transducers of array 11, and the amount of energy to be supplied to each of the transducers in array 11. Electronics network 93 responds to output signals of the transducers of array 11 to derive input signals for multi-B-scan cathode ray tube display 95. As described in detail infra, the B-scan display derived by cathode ray tube 95 is an x-y plot, wherein transducer number is an x-direction coordinate, the depth of a reflection from ? particular transducer is a y-axis coordinate, and the brightness of each point along a particular y-axis directed strip indicates the reflected energy amplitude from the corresponding depth.

The apparatus illustrated in FIG. 1 also includes a conventional two-dimensional imaging electronic readout system 96 for supplying signals to and reading signals from imaging transducers 53-56 of array 52. Imaging system 96 supplies signals to motor 62 to rotate the transducers of array 52 relative to axis 58. In addition, imaging system 96 supplies ultrasonic frequency electric energy to transducers 53-56 and responds to the energy reflected back to these transducers to derive a two-dimensional image, in a manner well known to those skilled in the art. The frequency of the electric signals supplied by imaging system 96 to transducers 53-56 and the frequency supplied by the transducers 53-56 to system 96 are considerably removed from the frequencies supplied to and derived from array 11. Initially imaging system 96 is operated to enable the operator to determine the exact location of the region to be treated so the focused far field of array 11 can be aimed at the region.

Figure 3:
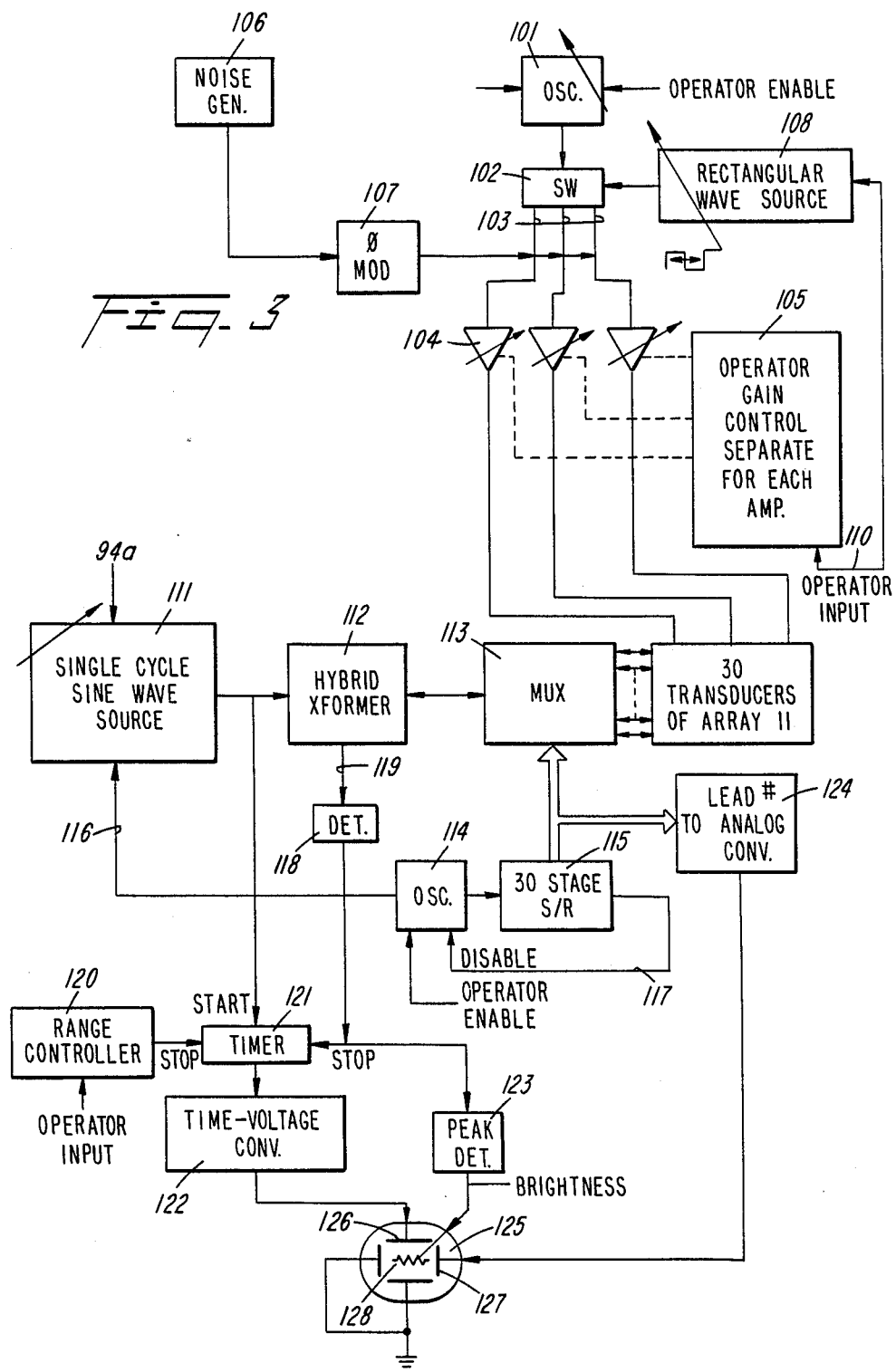
FIG. 3 is a block diagram of electronic circuitry included in the apparatus illustrated in FIG. 1.

Reference is now made to FIG. 3 of the drawing, a block diagram of the apparatus included in electronics network 93, FIG. 1. During treatment of a subject, the 30 transducers of array 11 are simultaneously responsive to bursts of electric signals having a carrier frequency in the range from 500 kilohertz to 1 megahertz and sufficient power to cause the transducers to derive focused far fields of hyperthermia compressional wave energy. To this end, variable frequency oscillator 101, having a center frequency of about 750 kilohertz and a relatively flat amplitude versus frequency characteristic from 500 kilohertz to 1 megahertz is provided. The amplitude vs. frequency responses of oscillator 101 and the transducers of array 11, as well as the circuitry connecting them, are such that the compressional wave energy derived from the transducers has a substantially constant amplitude over the 500 kilohertz–1 megahertz range, as illustrated in FIG. 5. The output frequency of oscillator 101 is fixed by a first of the operator inputs from source 94. The oscillator frequency is set to the high, middle and low ends of the frequency range to treat tissue close to table 15, at an intermediate position from the table, and remote from the table, respectively; i.e., close to the skin of the subject, at an intermediate region in the subject and far from the skin of the subject. Oscillator 101 is also responsive to a second one of the operator inputs from source 94, to energize the oscillator into an active state in which it derives a significant amount of output power. Oscillator 101 stays in the active state for a predetermined time interval, which an be set by an operator input from source 94; alternatively a further one of the operator inputs from source 94 is used to disable oscillator 101 if the operator decides that the oscillator should be turned off because, for example, the patient is experiencing pain from the ultrasonic compressional wave energy supplied to the patient by array 11.

The output of oscillator 101 is coupled to switch 102 which selectively supplies the oscillator output to lead 103. Switch 102 is energized on a periodic basis, such as once every millisecond, by the output of rectangular wave generator 108. Switch 102 is opened and closed for variable times to provide a variable duty cycle output of oscillator 101 on lead 103. To this end, the operator controls the trailing edge time position of each "half cycle" of the output of rectangular wave source 108 relative to the periodic leading edge time position thereof. Varying the trailing edge time position controls the duty cycle of the AC output of oscillator 101 coupled to lead 103. Switch 102 transmits the oscillator signal to lead 103 when the output of rectangular wave source 108 is high and blocks the signal otherwise. Because of the nonlinear, approximately square law relationship between the peak power or intensity output of a transducer and the effectiveness of a beam from the transducer on the treated region of the subject, low duty cycle energy on lead 103 enables much higher intensity peak power to be supplied to and derived from a particular transducer of array 11 without subjecting the subject to pain that is attained with continuous wave energy. For example if the duty cycle of the AC energy on lead 103 is 50%, the peak power which can be supplied by a transducer of array 11 to the patient is increased by a factor of two relative to the peak power which could be supplied by a transducer of array 11 for continuous wave, 100% duty cycle energy having the same average energy. As previously explained the effectiveness of the energy supplied to the treated area by the transducer is thus increased in a non-linear fashion without increasing the average energy. Moreover the increased absorption of energy in the tumor may actually reduce the energy absorption at remote bone pain sites, thereby decreasing the pain a subject would experience compared to the pain the subject would experience with 100% duty cycle energy of the same average power. Conversely, if the subject is experiencing pain at 100% duty cycle, the effectiveness of the treatment remains high by reducing the amount of energy supplied by the transducer to the subject in half to possibly prevent the patient from experiencing pain. The energy reduction is attained by maintaining the peak power output of the transducer constant and reducing the duty cycle to 50%. For a typical situation wherein there is a 30% duty cycle and the frequencies of sources 101 and 108 are respectively 1 megahertz and 100 kilohertz, three 1 megahertz sine wave cycles are coupled to lead 103 followed by a 0.7 millisecond interval during which there are no variations on lead 103, after which the 1 megahertz waves are again applied to the lead.

To enable the power of the hyperthermia compressional waves from array 11 to be increased as the duty cycle thereof decreases to maintain the energy from the array substantially constant, variable gain, power amplifiers 104 are cascaded with the output of oscillator 101. The gain of amplifiers 104 is controlled by computer coupling 110 which is set by the operator. The operator sets the gain of the amplifier inversely proportional to the duty cycle of the output of oscillator switch 102. To this end, coupling 110 is provided between a duty cycle control of rectangular wave source 108 and a gain control of amplifiers 104.

The variable duty cycle, variable amplitude AC power having a frequency in the range of 500 kilohertz to 1 megahertz is applied in parallel to transducers 20–49 by way of 30 different wide band, high power, variable gain AC amplifiers 104, one of which is provided for each of the transducers of array 11. Each of amplifiers 104 has a relatively flat response over the 500 kilohertz to 1 megahertz bandpass of transducers 20–49. The gain of each of amplifiers 104 is individually controlled by gain control network 105. Typically, gain control network 105 includes 30 computer controlled different potentiometers, each having an output controlled by a separate operator input from source 94, to control the gain of each of amplifiers 104. The operator sets the control on each of the potentiometers in network 105 to a setting suitable for the area being irradiated by the energy derived from its corresponding transducer connected to the output of the corresponding amplifier 104. If the beam from a particular transducer passes through a region which is susceptible to severe pain in response to ultrasonic energy derived from that transducer, the gain of the amplifier 104 connected to that particular transducer is reduced considerably relative to the gain of other amplifiers connected to other transducers in the array, or in the extreme may be set to zero.

The variable amplitude, variable frequency and variable duty cycle AC outputs of amplifiers 104 are applied to the transducers 20–49 of array 11 which are individually connected to each amplifier. The far fields of the transducers of array 11 irradiate a region where the transducers are focused.

To incoherently irradiate the region on which the combined far fields of the different transducers of array 11 are incident, the phase of the output signal of switch 102 from oscillator 101 is randomly varied, i.e., random angle modulation is imposed on the input of amplifiers 104. To this end, Gaussian noise source or generator 106 is provided. The output of Gaussian noise source 106 is applied to phase modulator 107, which responds to the randomly varying output of the generator to control the phase of the inputs to amplifiers 104 in a random manner. A similar effect can be accomplished by random variation of the oscillator 101 frequency by computer control initiated by the operator. The outputs of amplifiers 104 randomly vary in phase with respect to each other in a manner set by the operator. Oscillator 101 has a randomly varying phase at the frequency of the oscillator set by the operator.

The random phase, fixed frequency outputs of amplifiers 104 are applied to the transducers of array 11, so that the far field region on which the outputs of the array transducers is incident is incoherently irradiated and spatially spread, particularly at the beam edges. Because of this random spatial spreading at the edge of each beam pattern from the individual transducers of array 11, the tendency for constructive and/or destructive interference in overlapping regions of different transducers in the body is avoided.

Figure 7:
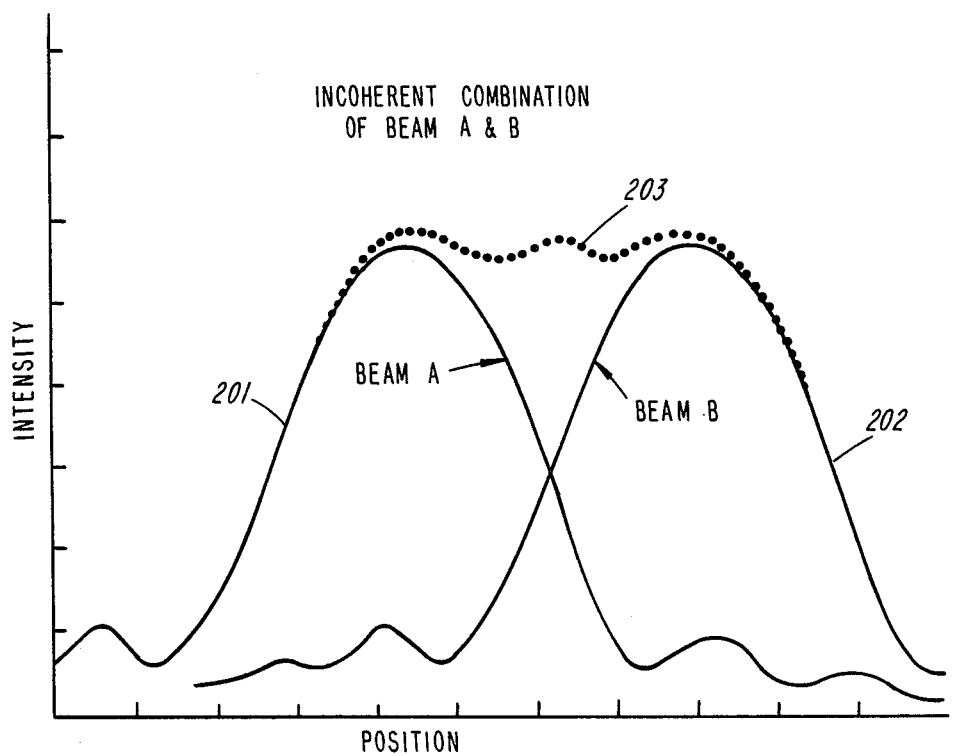
FIG. 7 is a plot of intensity vs. position for the combination of a pair of incoherently modulated beams.

The spatial relationship for a typical pair of incoherent beams A and B is illustrated in FIG. 7, wherein the intensity vs. position relationship of coherent beams A and B is illustrated by solid line traces 201 and 202. In the overlapping region of coherent beams A and B there is constructive and destructive interference so that the average combined intensities of beams A and B is approximately equal to the intensity of only one beam. By incoherently modulating the intensities of beams A and B, the steep skirts of traces 201 and 202 are combined in the overlapping region to produce dotted line trace 203, having a relatively constant amplitude from the peak of trace 201 to the peak of trace 202. A similar result can be achieved by replacing oscillator 101 with a narrow bandwidth frequency modulated oscillator.

Prior to the operator enabling oscillator 101 into an operative treating mode and after array 11 has been properly positioned to direct the far field at the treated region, transducers 20-49 of array 11 are sequentially energized with a single cycle of ultrasonic energy at the same frequency as the frequency of oscillator 101 to establish a multi-B-scan trace. The results of the B-scan trace are used by the operator to set the gain of amplifiers 104 and the position of the trailing edge of the output of rectangular wave source 108, which in turn controls the amplitude and duty cycle of the ultrasonic compressional wave treating energy derived from array 11.

To these ends, the operator, via source 94, sets single cycle sine wave source 111 to a "frequency" between 500 kilohertz and 1 megahertz. Source 111 thus derives one cycle of a sine wave having a period between two microseconds and one microsecond. The amplitude of the output of source 111 is the same for all "frequencies" in the 500 kilohertz to 1 megahertz region. The output of source 111 is sequentially coupled to each of transducers 20-49 of array 11 by way of hybrid transformer 112 and multiplexer 113. Single cycle AC source 111 may take any suitable form, such as a shock excited tank circuit including a parallel inductance and capacitor connected via a first switch to a DC power supply. A second switch short circuits the parallel inductance and capacitance in response to detection of the completion of a single cycle of an AC sine wave, as indicated by the output of a negative going zero crossing detector. Single or multiple output pulses may also be produced by digitly driven and controlled electronics. The sources 94 and 111 and oscillator 101 are controlled such that array 11 transducers are driven by only one source during alternate periods of heating and B-multi mode operation.

Derivation of the single cycle sine waves from source 111 is synchronized with coupling of the single cycle sine waves to the 30 different transducers of array 11. The time interval between adjacent single cycle sine waves derived from source 111 is determined by the maximum time required for a compressional wave from the transducers of array 11 to propagate to a site in the patient and be reflected back to the array transducers.

Oscillator 114 and 30 stage register 115 control the energization of source 111 and the application of single cycle sine waves from source 111 to each of the 30 transducers of array 11 in sequence. Oscillator 114 has a frequency sufficient to enable a single cycle of source 111 to be coupled to the transducers of array 11 and for the compressional wave energy derived from the selected transducer of the array to propagate to any site in the patient and for the reflected energy from the patient site to propagate back to the array and to provide for processing for such a signal. Oscillator 114 continues to derive enabling pulses for source 111 until all 30 transducers of array 11 have been supplied with a single cycle sine wave from source 111.

To these ends, the output of oscillator 114 is coupled via lead 116 to source 111. In response to the leading edge or zero crossing of the wave derived by source 111, the switch of source 111 connected between the shock excited tank circuit and a DC power supply therefor is closed; alternatively, digitally controlled electronics (not shown) are triggered to cause a single cycle to be derived from the source. Each stage of shift register 115 includes an output lead which is coupled to an enable input of a different one of the switches in multiplexer 113. Multiplexer 113 includes 30 switches, each having a first signal terminal connected in parallel to a terminal of hybrid transformer 112. Each of the 30 switches in multiplexer 113 has a second terminal connected to a corresponding transducer of array 11.

Shift register 115 is stepped stage by stage in response to each cycle derived by oscillator 114, in synchronism with derivation of the single cycle sine waves of source 111. Thereby, the first signal terminal of multiplexer 113 is sequentially coupled to each of the second signal terminals of the multiplexer and to the 30 transducers of array 11. The outputs of shift register 115 are coupled to an enable input of multiplexer 113 to cause the switches of the multiplexer to remain in a closed state for a sufficient time to couple a single cycle from source 111 to one of the transducers of array 11, and to enable the reflected energy coupled back to that transducer from the site to be supplied back through the multiplexer to hybrid transformer 112, as well as to provide processing time for the signal derived by the transducer in response to the reflected energy. In a response to shift register 115 being driven by oscillator 114 to the last stage of the shift register, the shift register supplies, via lead 117, a pulse to a disable input of oscillator 114. The transducers of array 11 are thus stepped through only one complete cycle of operation each time that oscillator 114 is enabled by a signal from operator input source 94. The operator can also request repetitive operation.

To enable the B-scan trace to be derived, the amplitude of the reflected energy coupled back to each transducer of array 11 is detected. The travel time of a single cycle of energy derived from a transducer of array 11 to a reflecting site in the patient and back to the particular transducer of the array is also monitored. An indication is provided of the number of the transducer in the array which is energized and with which the amplitude and travel time indications are associated. To determine the amplitude of the reflected energy incident on a particular transducer of the array which has been supplied with a single cycle by sine wave source 111, the transducer which has been supplied with the single cycle by source 111 remains connected to hybrid transformer 112 by multiplexer 113, because of the previously described operation of register 115. A replica of the reflected compressional wave energy incident on the particular transducer of array 11 is coupled from a second signal terminal of multiplexer 113 to the multiplexer first signal terminal, thence to hybrid transformer 112 which drives amplitude detector 118 via lead 119. Amplitude detector 118 derives an output signal proportional to the ultrasonic frequency peak amplitude of the reflected compressional wave incident on the transducer of array 11.

The output pulse of detector 118 is shaped and used to modulate the brightness of the image of CRT 125. The range controller 120 supplies a "stop" input signal to timer 121, which has a "start" input responsive to the output of oscillator 114 that triggers single cycle sine wave source 111. Timer 121 responds to the signals supplied to the start and stop inputs thereof to derive a square wave having leading and trailing edges respectively synchronized with the derivation of each single cycle sine wave derived from source 111 and the trailing edge at the end of the set range signal from range controller 120. Hence, the leading and trailing edges of the square wave derived by timer 121 can be considered as indicative of the travel time of a compressional wave from a transducer of array 11 to a reflecting site in the subject and the travel time of the reflected compressional wave back from the site to the particular transducer. The rectangular wave output of timer 121 is converted into a variable amplitude wave having a magnitude proportional to the travel time by time-voltage converter 122; typically converter 122 is a source of linear sawtooth waves, wherein the sawtooth is initiated and terminated in response to the leading and trailing edges of the output of timer 121, respectively.

To indicate the amplitude of the reflected energy incident on each of the transducers of array 11, from the several possible reflecting sites in the path of the beam of each transducer the output of detector 118 is supplied to peak (positive and negative) detector network 123 which maintains a constant output level between adjacent peak outputs of detector 118. Network 123 drives the brightness control input of scope 125 with one or more different amplitudes while the travel time indicating signal is derived by converter 122.

An analog voltage is derived to indicate the number of the transducer in array 11 which is energized by single cycle sine wave source 111 and which supplies a signal back to detector 118 via hybrid transformer 112 and multiplexer 113. To these ends, the 30 output leads of 30 stage shift register 115 are coupled to lead number-to-analog converter 124. Converter 124 derives a variable amplitude analog output voltage having a value directly proportional to the number of the stage in shift register 115 which is supplying an enable signal to a particular switch in multiplexer 113.

The multi B-scan trace is produced by cathode ray tube 125 in response to the output signals of time-voltage converter 122, network 123, and lead number to analog converter 124. The output signals of converters 122 and 124 are respectively applied to the y and x axis electrodes 126 and 127 of cathode ray tube 125, while the intensity of the cathode ray beam derived by storage cathode ray tube 125 is controlled by the amplitude of the output of network 123, as applied to grid 128 of the cathode ray tube. Cathode ray tube 125 includes a phosphorous face with sufficient storage capability to maintain the image written on it by the cathode ray beam for many seconds. Thereby, the operator is provided with a B-scan display for a considerable time period after oscillator 114 has been disabled and while no single cycle sine waves are being supplied by source 111 to the transducers of array 11. Alternatively, well known computer based storage techniques can be used to maintain the image on tube 25.

Reference is now made to FIG. 6 of the drawing, an exemplary multi-B-scan display for the 30 transducers of array 11. In FIG. 6, transducer number is plotted in the x-direction while the distance between the plane of array 11 and the site reflecting energy back to the array is indicated in the y-direction. Thus, there are essentially 30 different strips extending parallel to the y-axis, one for each of the transducers of array 11. The brightness at each point of each strip provides an indication of the amplitude of the reflected energy coupled back to each energized transducer in the array from the reflecting site.

An experienced operator can determine from the distribution of brightness along each stripe whether the reflected energy associated with the particular transducer is from an air-tissue interface or from a tissue-tissue interface or from bone in the patient. The operator uses source 94 to control the gain of the particular amplifier 104 associated with a transducer so that a particular transducer emitting energy which is incident on bone is supplied by oscillator 101 with a relatively low amplitude signal, or if necessary, a zero amplitude signal. This prevents the patient from being subjected to pain during the treatment process because the compressional wave energy from the transducers of array 11 is basically decoupled from the areas containing bone or those areas which are subjected to compressional wave energy having sufficiently low amplitude as to not induce substantial pain in the patient.

While there has been described and illustrated one specific embodiment of the invention, it will be clear that variations in the details of the embodiment specifically illustrated and described may be made without departing from the true spirit and scope of the invention as defined in the appended claims.

I claim:

1. A method of treating a region of a subject with compressional wave energy derived from an array of ultrasonic transducers having a focused far field and a wide band pass frequency response and for analyzing matter of the subject in the path between the transducers and the region comprising the steps of from time to time exciting the transducers with pulse like ultrasonic electric energy having substantial frequency components in the band pass of the transducers, the transducers being excited while the region is in the focused far field of the array, the frequency and the transducer response being such that said frequency components are incident on the subject during said exciting step, the pulse like ultrasonic compressional wave energy from said transducers being reflected from certain regions internally of the subject back to the transducers while the transducers are no longer excited by the pulse like electric energy whereby the transducers derive electric signals having time positions and amplitudes together enabling information about different volumes in the subject between the array and the region to be determined, responding to the time positions of the derived electric signals to display the information, and supplying many cycles of treating hyperthermia ultrasonic electric energy to the transducers in the treating period between tow consecutive periods when the pulse like electric energy is exciting the transducers and the electric signals are being derived, the many cycles of ultrasonic electric energy being periodically disrupted for at least several cycles thereof and being supplied to the transducers while the region is in the focused far field and causing the transducers to be excited to derive in the subject many cycles of treating hyperthermia ultrasonic compressional wave energy having a frequency in the band pass of the transducers and having a duty cycle less than one, said method including the step of varying the duty cycle and amplitude of the compressional wave energy of at least one of said transducers in an inverse manner.

2. The method of claim 1 wherein the pulse like energy has a substantially single cycle sine wave like waveshape, further including the step of adjusting the periods of the single cycle and the treating energy so they are approximately the same while the same region is in the focused far field.

3. The method of claim 1 further comprising the step of incoherently modulating the far field by randomly phase modulating the treating ultrasonic electric energy applied to the transducers so that adjacent beams from different ones of said transducers in the focused far field spatially overlap to a greater extent than coherent adjacent focused far field beams.

4. The method of claim 1 further comprising the step of controlling the duty cycle of the treating compressional wave energy and the amplitude of the treating compressional wave energy derived from different transducers in the array to minimize pain experienced by the subject due to the compressional wave energy being incident on different portions of the subject while maintaining the energy of the treating compressional wave energy substantially constant.

5. The method of claim 1 wherein different ones of the transducers are excited in sequence whereby pulse like compressional wave energy from the different transducers is incident on the subject and reflected from the certain regions at different times, detecting the interval from the time one of said transducers derives one of the pulse like waves to the time said pulse like wave is reflected back to the array, detecting the amplitude of each pulse like wave reflected back to the array for each different one of said transducers, and displaying along mutually orthogonal first and second axes of an x-y display the number of each transducer deriving a pulse like wave of the compressional wave energy and the detected time interval associated with each numbered transducer respectively, and displaying on said display an indication of the detected amplitude associated with each numbered transducer.

6. The method of claim 5 further comprising adjusting the amplitude of the treating energy applied to each different transducer in response to the displayed information.

7. The method of claim 1 wherein different ones of the transducers are excited in sequence whereby pulse like compressional wave energy from the different transducers is incident on the subject and reflected from the certain regions at different times, detecting the amplitude of each pulse like wave reflected back to the array, and adjusting the amplitude of the treating energy applied to each different transducer in response to the detected amplitude for the associated different transducer.

8. A method of treating regions located close to and far from the surface of the skin of a subject with compressional wave energy from an array of ultrasonic transducers having a focused far field and a wide bandpass comprising the steps of treating a region close to the skin of the subject by focusing the far field of the array at one of said regions located close to the skin of said subject, and then exciting the transducers with electric energy such that the transducers derive in the subject many cycles of region treating ultrasonic compressional wave energy at a frequency within the band pass and relatively close to a high frequency cut off of the bandpass, treating a region far from the skin of the subject by focusing the far field of the array at one of said regions located far from the skin of said subject, and then exciting the transducers with electric energy such that the transducers derive in the subject many cycles of region treating ultrasonic compressional wave energy at a frequency within the band pass and relatively far from the high frequency cut off of the band pass, said method including the step of varying the duty cycle and amplitude of the compressional wave energy of at least one of said transducers in an inverse manner.

9. The method of claim 8 further comprising the step of controlling the duty cycle and the amplitude of the treating compressional wave energy of one or more of said transducers to minimize pain experienced by the subject due to the compressional wave energy being incident on different portions of the subject.

10. The method of claim 8 further comprising the step of controlling the duty cycle of the treating compressional wave energy and individually controlling the amplitude of the treating compressional wave energy derived from the transducers in the array to minimize pain experienced by the subject due to the compressional wave energy being incident on different portions of the subject.

11. The method of claim 10 further comprising the step of controlling the duty cycle of the treating compressional wave energy and the amplitude of the treating compressional wave energy derived from different transducers in the array to minimize pain experienced by the subject due to the compressional wave energy being incident on different portions of the subject while maintaining the energy of the treating compressional wave energy substantially constant.

12. A method of treating a region in a subject with treating hyperthermia compressional wave energy from an array of ultrasonic transducers having a focused far field comprising the steps of focusing the far field of the array at the region, and then simultaneously exciting transducers of the array with electric energy having a duty cycle considerably less than one such that each of the transducers derives in the subject a beam of hyperthermia treating focused far field ultrasonic compressional wave energy having said duty cycle, said method further including inversely varying the intensity and duty cycle of the treating energy applied to at least some of the transducers.

13. The method of claim 12 further comprising the step of incoherently modulating the far field by random phase modulating said electric energy so that adjacent beams from different ones of said transducers in the focused far field spatially overlap to a greater extent than coherent adjacent focused far field beams.

14. The method of claim 12 further comprising the step of controlling the duty cycle and the amplitude of the treating compressional wave energy to minimize pain experienced by the subject due to the compressional wave energy being incident on different portions of the subject.

15. A method of treating a region in a subject with treating hyperthermia compressional wave energy from an array of ultrasonic transducers having a focused far field comprising the steps of focusing the far field of the array at the region, supplying electric energy to said transducers, and varying the duty cycle and amplitude of said electric energy for at least one of said transducers in an inverse manner.

* * * * *